US00PP13769P29

(12) United States Plant Patent
Oudshoorn

(10) Patent No.: US PP13,769 P2
(45) Date of Patent: May 6, 2003

(54) ECHINACEA PLANT NAMED 'JADE'

(75) Inventor: Hubertus Gerardus Oudshoorn, Rijpwetering (NL)

(73) Assignee: Future Plants V.O.F., Lisserbroek (NL)

( * ) Notice: Subject to any disclaimer, the term of this patent is extended or adjusted under 35 U.S.C. 154(b) by 0 days.

(21) Appl. No.: 10/139,965

(22) Filed: May 6, 2002

(51) Int. Cl.[7] ..... A01H 5/00
(52) U.S. Cl. ..... Plt./263
(58) Field of Search ..... Plt./263

(56) References Cited

U.S. PATENT DOCUMENTS

PP12,242 P2 * 12/2001 Hawks ..... Plt./263

OTHER PUBLICATIONS

UPOV ROM GTITM Computer Database, GTI JOUVE retrieval software 2002/02, citation(s) for 'Jade'.*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of Echinacea plant named 'Jade', characterized by its upright and somewhat outwardly spreading plant habit; freely basal branching growth habit; freely flowering habit and white-colored ray florets and green-colored disc florets.

1 Drawing Sheet

BOTANICAL CLASSIFICATION/CULTIVAR DESIGNATION

*Echinacea purpurea* cultivar Jade.

BACKGROUND OF THE INVENTION

The present Invention relates to a new and distinct cultivar of Echinacea plant, botanically known as *Echinacea purpurea*, and hereinafter referred to by the name 'Jade'.

The new Echinacea was discovered as a chance seedling of two unidentified selections of *Echinacea purpurea*, not patented. The new Echinacea was discovered and selected by the Inventor in 1995 as a single flowering plant in a controlled environment in Rijpwetering, The Netherlands.

Asexual reproduction of the new Echinacea by divisions was first conducted in Rijpwetering, The Netherlands in 1995. Since then, asexual reproduction by divisions has shown that the unique features of this new Echinacea are stable and reproduced true to type in successive generations.

SUMMARY OF THE INVENTION

The cultivar Jade has not been observed under all possible environmental conditions. The phenotype may vary somewhat with variations in environment such as temperature and light intensity without, however, any variance in genotype.

The following traits have been repeatedly observed and are determined to be the unique characteristics of 'Jade'. These characteristics in combination distinguish 'Jade' as a new and distinct Echinacea:

1. Upright and somewhat outwardly spreading plant habit.
2. Freely basal branching growth habit.
3. Freely flowering habit.
4. White-colored ray florets and green-colored disc florets.

Plants of the new Echinacea differ primarily from plants of the parent selections in ray and disc floret coloration.

Plants of the new Echinacea can be compared to plants of the Echinacea cultivar White Lustre, not patented. However, plants of the new Echinacea have more inflorescences per lateral stem than plants of the cultivar White Lustre. In addition, plants of the new Echinacea and the cultivar White Lustre differ in ray and disc floret coloration.

BRIEF DESCRIPTION OF THE PHOTOGRAPH

The accompanying colored photograph illustrates the overall appearance of the new Echinacea showing the colors as true as it is reasonably possible to obtain in colored reproductions of this type. Colors in the photograph may differ from the color values cited in the detailed botanical description which accurately describe the colors of the new Echinacea. The photograph comprises a side perspective view of several typical flowering plants of 'Jade' grown in an outdoor nursery.

DETAILED BOTANICAL DESCRIPTION

The aforementioned photograph and following observations and measurements describe plants grown in Lisserbroek, The Netherlands, in an outdoor nursery under full sun conditions. In August, when plants were about two years old, the photograph and the observations and measurements were taken. Color references are made to The Royal Horticultural Society Colour Chart, 2001 edition, except where general terms of ordinary dictionary significance are used.

Botanical classification: *Echinacea purpurea* cultivar Jade.
Parentage:

*Female, or seed, parent.*—Unidentified selection of *Echinacea purpurea*, not patented.

*Male, or pollen, parent.*—Unidentified selection of *Echinacea purpurea*, not patented.

Propagation:

*Type.*—By divisions.

*Time to produce a rooted plant.*—About two months.

*Root description.*—Fine, fibrous and well-branched.

Plant description:

*Appearance.*—Perennial herbaceous container and garden plant. Upright and somewhat outwardly spreading plant habit; narrow inverted triangle. Freely basal branching; basal branches with about three lateral branches each; dense and full plants. Moderately vigorous growth habit.

*Plant height.*—About 75 cm.

*Plant width or area of spread.*—About 60 cm.

*Lateral branches.*—Length: About 27 cm. Diameter: About 4 mm. Internode length: About 4 cm. Aspect: Upright to slightly outward. Strength: Strong. Texture: Sparsely pubescent; rough. Color: 144A.

*Foliage description.*—Arrangement: Alternate; single. Length: About 13 cm. Width: About 4.7 cm. Shape: Lanceolate. Apex: Acute. Base: Attenuate. Margin: Entire with occasional irregular serrations. Venation pattern: Pinnate. Texture, upper and lower surfaces: Pubescent; rough. Color: Young foliage, upper surface: 137A. Young foliage, lower surface: 137C. Fully expanded foliage, upper surface: 139A. Fully expanded foliage, lower surface: 137B. Venation, upper and lower surfaces: 144C. Petiole: Length: About 1.7 cm. Diameter: About 2.5 mm. Texture, upper and lower surfaces: Smooth. Color, upper and lower surfaces: 144A to 144B.

Inflorescence description:

*Appearance.*—Terminal and axillary inflorescences held mostly above and beyond the foliage on strong peduncles. Composite inflorescence form, radially symmetrical; oblanceolate-shaped ray florets; disc florets massed at the center; ray and disc florets arranged acropetally on a capitulum. Inflorescences persistent. Inflorescences face mostly upright.

*Flowering response.*—Plants flower continuous and freely from late July to late September in Lisserbroek, The Netherlands.

*Postproduction longevity.*—Inflorescences maintain good color and substance for about five days on the plant when grown in an outdoor environment. As a cut flower, inflorescences maintain good color and substance for about two weeks in an interior environment.

*Quantity of inflorescences.*—Freely flowering; about twelve open inflorescences per plant at one time.

*Fragrance.*—Faint, sweet.

*Inflorescence bud* (*at stage of showing color*).—Length: About 5 mm. Diameter: About 1 mm. Shape: Narrowly ovoid. Color: 141A.

*Inflorescence size.*—Diameter: About 9 cm. Depth (height): About 3.4 cm. Disc diameter: About 3.5 cm.

*Ray florets.*—Length: About 3.9 cm. Width: About 1.2 cm. Shape: Oblanceolate. Apex: Emarginate. Base: Acute. Margin: Entire. Texture: Smooth. Orientation: Initially upright then perpendicular to the peduncle. Number of ray florets per inflorescence: About 20 in a single whorl. Color: When opening and fully opened, upper surface: 157A. When opening and fully opened, lower surface: 150D; towards the apex, irregular longitudinal stripes, 144B to 144C to 143C.

*Disc florets.*—Shape: Tubular, elongated. Apex: Five-pointed; acute. Length: About 8 mm. Width: About 1.5 mm. Number of disc florets per inflorescence: More than 200. Color, immature and mature: 144B to 144C; towards the apices, 143A to 143B.

*Phyllaries.*—Length: About 7 mm. Diameter: About 2 mm. Shape: Lanceolate. Apex: Narrowly acute. Base: Fused. Margin: Entire. Texture: Densely pubescent. Number per inflorescence: About 20 in about four whorls. Color, upper and lower surfaces: 137B.

*Peduncles.*—Length: About 17 cm. Diameter: About 4 mm. Angle: Mostly erect. Strength: Strong. Texture: Sparsely pubescent; rough. Color: 144A.

*Reproductive organs.*—Androecium: Present on disc florets only. Stamen number: Three per floret; basifixed. Anther shape: Oblong. Anther length: About 1 mm. Anther color: 151C. Pollen amount: Moderate. Pollen color: 14A. Gynoecium: Present on both ray and disc florets. Pistil number: One per floret. Pistil length: About 6 mm. Stigma shape: Two-parted. Stigma color: 144A. Style length: About 5 mm. Style color: 144A. Ovary color: 145C.

*Fruit.*—Type: Flattened achene. Quantity per inflorescence: One. Length: About 8 mm. Diameter: About 1 mm. Color: 161B.

*Seed.*—Yield: Low, about 5 percent of inflorescences produce viable seed. Quantity of seed per fruit: One. Length: About 2 mm. Diameter: About 1 mm. Color: N199B.

Disease/pest resistance: Resistance to pathogens and pests common to Echinaceas has not been observed on plants grown under outdoor conditions.

Temperature tolerance: Plants of the new Echinacea have been observed to tolerate temperatures from about −12 to 35° C.

It is claimed:

1. A new and distinct cultivar of Echinacea plant named 'Jade', as illustrated and described.

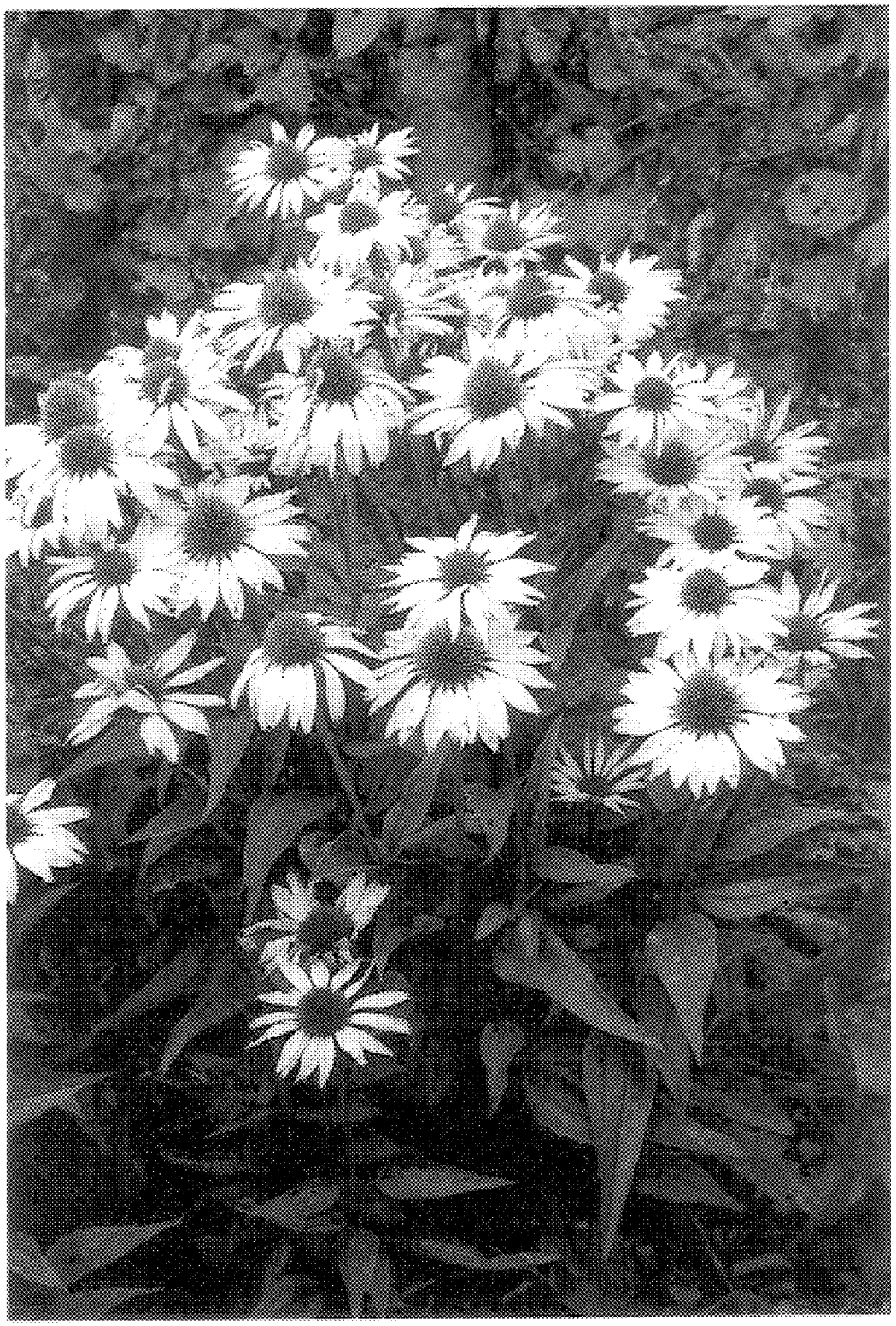

* * * * *